United States Patent
Krieger et al.

(10) Patent No.: US 10,918,408 B2
(45) Date of Patent: Feb. 16, 2021

(54) CUTTING DEVICES AND METHODS

(71) Applicant: Cook Medical Technologies LLC, Bloomington, IN (US)

(72) Inventors: Joshua F. Krieger, Bloomington, IN (US); Ram H. Paul, Bloomington, IN (US); Zachary Berwick, Indianapolis, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 315 days.

(21) Appl. No.: 15/727,791

(22) Filed: Oct. 9, 2017

(65) Prior Publication Data

US 2018/0028216 A1 Feb. 1, 2018

Related U.S. Application Data

(62) Division of application No. 14/600,336, filed on Jan. 20, 2015, now Pat. No. 9,782,191.

(Continued)

(51) Int. Cl.
*A61B 17/32* (2006.01)
*B21F 45/00* (2006.01)
*A61B 17/00* (2006.01)

(52) U.S. Cl.
CPC ...... *A61B 17/320016* (2013.01); *A61B 17/32* (2013.01); *B21F 45/008* (2013.01); *A61B 2017/00526* (2013.01)

(58) Field of Classification Search
CPC ......... B21B 2263/04; B21C 3/18; B21D 3/02; B21F 45/12; B21F 45/22; B21K 5/00; B21K 11/00
See application file for complete search history.

(56) References Cited

U.S. PATENT DOCUMENTS 515,347 A * 2/1894 Manville .................. B21F 1/00
140/80
2,379,886 A * 7/1945 De Witt .................. B21F 45/12
29/9

(Continued)

FOREIGN PATENT DOCUMENTS

EP 0321132 6/1989
EP 0511323 11/1992

(Continued)

OTHER PUBLICATIONS

Mustad Slow Death Hooks, Product Catalog Americas 2014, Jul. 1 2013, https:www.flipsnack.com/manichov/americas-catalog-2014.html (retrieved Jun. 3, 2020), p. 14 (Year: 2013).*

(Continued)

*Primary Examiner* — Adam J Eiseman
*Assistant Examiner* — Stephen Floyd London
(74) *Attorney, Agent, or Firm* — MacMillan, Sobanski & Todd, LLC (57) ABSTRACT

Cutting devices useful for cutting objects or materials are described. Examples of cutting devices useful for creating avulsions in animals, such as human beings, are described. A cutting device includes an elongate main body having proximal and distal ends. A first portion of the main body has a cross-sectional shape that substantially lacks flat surfaces and a second portion of the main body has a cross-sectional shape having one, two or more flat surfaces. The distal end defines a hook having one or more sharpened edges disposed within the notch of the hook. Methods of making cutting devices are also described.

17 Claims, 4 Drawing Sheets

Related U.S. Application Data (60) Provisional application No. 61/929,652, filed on Jan. 21, 2014.

(56) References Cited

U.S. PATENT DOCUMENTS

| | | | |
|---|---|---|---|
| 2,779,334 A | 1/1957 | Sandbom | |
| 2,863,458 A | 12/1958 | Modney et al. | |
| 3,038,475 A * | 6/1962 | Orcutt | A61B 17/06066 606/223 |
| 3,268,428 A * | 8/1966 | Buccino | B21G 1/12 205/664 |
| 3,508,553 A | 4/1970 | Kanbar et al. | |
| 3,608,544 A | 9/1971 | Schnepper | |
| 3,837,345 A | 9/1974 | Matar | |
| 3,986,493 A | 10/1976 | Hendren, III | |
| 4,493,321 A | 1/1985 | Leather | |
| 4,528,982 A | 7/1985 | Wellenstam | |
| D282,965 S | 3/1986 | Wellenstam | |
| 4,655,217 A | 4/1987 | Reed | |
| 4,739,760 A | 4/1988 | Chin et al. | |
| 4,768,508 A | 9/1988 | Chin et al. | |
| 4,791,913 A | 12/1988 | Maloney | |
| 4,905,402 A * | 3/1990 | Clark | A01K 83/00 43/43.16 |
| 4,952,215 A | 8/1990 | Ouriel et al. | |
| 5,011,489 A | 4/1991 | Salem | |
| 5,049,154 A | 9/1991 | Quadri | |
| 5,069,679 A | 12/1991 | Taheri | |
| 5,087,264 A | 2/1992 | Miller et al. | |
| 5,092,872 A | 3/1992 | Segalowitz | |
| 5,133,725 A | 7/1992 | Quadri | |
| 5,139,506 A | 8/1992 | Bush | |
| 5,141,491 A | 8/1992 | Bowald | |
| 5,171,316 A | 12/1992 | Mehigan | |
| 5,234,450 A | 8/1993 | Segalowitz | |
| 5,263,974 A * | 11/1993 | Matsutani | A61B 17/00 606/222 |
| 5,284,478 A | 2/1994 | Nobles et al. | |
| 5,304,189 A | 4/1994 | Goldberg et al. | |
| D351,022 S | 9/1994 | Saito | |
| 5,352,232 A | 10/1994 | Cohen | |
| 5,380,304 A | 1/1995 | Parker | |
| 5,443,474 A | 8/1995 | Sfakianos | |
| 5,514,151 A | 5/1996 | Fogarty et al. | |
| 5,522,824 A | 6/1996 | Ashby | |
| 5,527,327 A | 6/1996 | Louw et al. | |
| 5,584,842 A | 12/1996 | Fogarty et al. | |
| 5,591,183 A | 1/1997 | Chin | |
| 5,601,581 A | 2/1997 | Fogarty et al. | |
| 5,624,455 A | 4/1997 | Matsuno | |
| 5,626,578 A | 5/1997 | Tihon | |
| 5,630,268 A * | 5/1997 | Smith | A61B 17/06066 163/5 |
| 5,658,282 A | 8/1997 | Daw et al. | |
| 5,658,301 A | 8/1997 | Lemaitre et al. | |
| 5,658,302 A | 8/1997 | Wicherski et al. | |
| 5,707,389 A | 1/1998 | Louw et al. | |
| 5,730,748 A | 3/1998 | Fogarty et al. | |
| 5,749,882 A | 5/1998 | Hart et al. | |
| 5,782,850 A | 7/1998 | Ro | |
| 5,843,102 A | 12/1998 | Kalmann et al. | |
| 5,846,241 A | 12/1998 | Kittur et al. | |
| 5,853,417 A | 12/1998 | Fogarty et al. | |
| 5,868,768 A | 2/1999 | Wicherski et al. | |
| 5,871,496 A | 2/1999 | Ginn et al. | |
| 5,876,413 A | 3/1999 | Fogarty et al. | |
| 5,899,913 A | 5/1999 | Fogarty et al. | |
| 5,947,994 A | 9/1999 | Louw et al. | |
| 5,997,557 A | 12/1999 | Barbut et al. | |
| 6,068,639 A | 5/2000 | Fogarty et al. | |
| 6,178,968 B1 | 1/2001 | Louw et al. | |
| 6,200,336 B1 | 3/2001 | Pavcnik et al. | |
| 6,253,485 B1 * | 7/2001 | Jilling | A01K 83/00 43/42.53 |
| 6,267,758 B1 | 7/2001 | Daw et al. | |
| 6,352,544 B1 | 3/2002 | Spitz | |
| 6,391,050 B1 | 5/2002 | Broome | |
| 6,451,035 B1 | 9/2002 | Fogarty et al. | |
| 6,508,833 B2 | 1/2003 | Pavcnik et al. | |
| 6,527,787 B1 | 3/2003 | Fogarty et al. | |
| 6,565,588 B1 | 5/2003 | Clement et al. | |
| 6,648,815 B2 | 11/2003 | Schoellhorn et al. | |
| 6,840,946 B2 | 1/2005 | Fogarty et al. | |
| 6,926,725 B2 | 8/2005 | Cooke et al. | |
| 7,037,316 B2 | 5/2006 | McGuckin, Jr. et al. | |
| 7,077,852 B2 | 7/2006 | Fogarty et al. | |
| 7,163,546 B2 | 1/2007 | Mirizzi et al. | |
| 7,473,262 B2 | 1/2009 | Fogarty et al. | |
| 7,485,125 B2 | 2/2009 | Sjostrom | |
| 7,651,503 B1 | 1/2010 | Coe et al. | |
| 7,695,470 B1 | 4/2010 | Stewart et al. | |
| 7,717,930 B2 | 5/2010 | Paul, Jr. et al. | |
| 7,744,617 B2 | 6/2010 | Lunsford et al. | |
| 7,887,558 B2 | 2/2011 | Lin et al. | |
| 8,062,317 B2 | 11/2011 | McGuckin, Jr. et al. | |
| 8,109,952 B2 | 2/2012 | Pikus et al. | |
| 8,246,641 B2 | 8/2012 | Osborne et al. | |
| 8,303,612 B2 | 11/2012 | Nakao et al. | |
| 8,372,097 B2 | 2/2013 | Buchbinder et al. | |
| 8,398,663 B2 | 3/2013 | Paul, Jr. et al. | |
| 8,449,566 B2 | 5/2013 | Finitsis | |
| 8,550,980 B2 | 10/2013 | Rane | |
| 8,613,752 B2 | 12/2013 | Kamel | |
| 9,198,681 B2 | 12/2015 | Plassman | |
| 9,782,191 B2 | 10/2017 | Krieger et al. | |
| 2003/0125759 A1 | 7/2003 | Mirizzi et al. | |
| 2003/0125795 A1 | 7/2003 | Pavcnik et al. | |
| 2003/0144670 A1 | 7/2003 | Pavcnik et al. | |
| 2004/0122472 A1 * | 6/2004 | Collier | C21D 9/26 606/222 |
| 2004/0167619 A1 | 8/2004 | Case et al. | |
| 2004/0186558 A1 | 9/2004 | Pavcnik | |
| 2004/0204730 A1 | 10/2004 | Goldberg et al. | |
| 2004/0260389 A1 | 12/2004 | Case et al. | |
| 2005/0076557 A1 * | 4/2005 | Fujii | A01K 83/00 43/43.16 |
| 2005/0192606 A1 | 9/2005 | Paul, Jr. et al. | |
| 2009/0101244 A1 * | 4/2009 | Ogawa | A01K 83/00 148/538 |
| 2009/0157116 A1 * | 6/2009 | Cichocki, Jr. | A61B 17/06066 606/223 |
| 2010/0234864 A1 * | 9/2010 | Keller | A61B 17/32 606/159 |
| 2010/0286719 A1 | 11/2010 | Paul et al. | |
| 2015/0201958 A1 | 7/2015 | Krieger et al. | |
| 2017/0188560 A1 * | 7/2017 | Graham | A01K 83/00 |

FOREIGN PATENT DOCUMENTS

| | | | |
|---|---|---|---|
| EP | 0558039 | 9/1993 | |
| EP | 0741544 | 11/1996 | |
| EP | 0772421 | 5/1997 | |
| GB | 1200345 A * | 7/1970 | B41F 45/12 |
| WO | WO198907914 | 9/1989 | |
| WO | WO1991001689 | 2/1991 | |
| WO | WO1992008414 | 5/1992 | |
| WO | WO1995019737 | 7/1995 | |
| WO | WO1995028888 | 11/1995 | |
| WO | WO1996033662 | 10/1996 | |
| WO | WO1996039950 | 12/1996 | |
| WO | WO1997014362 | 4/1997 | |
| WO | WO1997016125 | 5/1997 | |
| WO | WO1997018767 | 5/1997 | |
| WO | WO1998024379 | 6/1998 | |
| WO | WO2005037345 | 4/2005 | |
| WO | WO2007134100 | 11/2007 | |

OTHER PUBLICATIONS

Lauten, et al., "Percutaneous caval stent valve implantation: investigation of an interventional approach for treatment of tricuspid (56) References Cited

OTHER PUBLICATIONS regugitation," European Heart Journal 31, pp. 1274-1281, (2010).
European Patent Office, European Search Report, for Application No. 15151968.3, dated Feb. 12, 2015, pp. 1-6.
European Patent Office. Examination Report for European patent application No. 15151968.3, dated Oct. 4, 2019, pp. 1-4.
European Patent Office. Examination Report for EP application No. 15151968.3, dated Mar. 25, 2020, p. 1-4.

* cited by examiner

CUTTING DEVICES AND METHODS

CROSS REFERENCE TO RELATED APPLICATIONS

This application is a division of U.S. patent application Ser. No. 14/600,336, filed on Jan. 20, 2015, now U.S. Pat. No. 9,782,191, and which claims the benefit of U.S. Provisional Application No. 61/929,652, filed on Jan. 21, 2014. The entire contents of each of these related applications is incorporated into this disclosure by reference.

FIELD

The disclosure relates to cutting devices. Particular embodiments are useful as medical devices for creating avulsions in animals, such as human beings. For example, embodiments are useful as medical devices in the removal of synechiae in the venous system. Embodiments are also useful for clipping chordae tendineae from surrounding heart tissue. Embodiments can be used for cutting non-biological material, also. For example, embodiments are useful for cutting sutures, tubular plastic sheaths, and other materials.

BACKGROUND

It is desirable to cut objects and materials in a variety of processes and contexts. For example, cutting of biological material, such as a tissue or other body structure, is sometimes desirable as part of a treatment process. For example, creation of an avulsion—an injury in which a body structure is detached from its normal point of attachment to another body structure—is sometimes performed to remove leaflets of an incompetent venous valve. Also, synechiae can be cut during management of post thrombotic syndrome and tendons and other connective tissues can be cut to reposition or remove a particular tissue. For example, in certain procedures, it may be desirable to clip the chordae tendineae. Cutting of non-biological material, such as plastics, is also desirable in a variety of processes and contexts, including the making and use of various medical devices.

There are several cutting devices and methods known in the art. A need remains, however, for improved devices and methods.

DESCRIPTION OF EXAMPLE EMBODIMENTS

The following detailed description and the appended drawings describe and illustrate various example embodiments of cutting devices and methods useful in creating avulsions in animals. The description and illustration of these examples are provided to enable one skilled in the art to make and use a cutting device useful in creating avulsions in animals. They are not intended to limit the scope of the claims in any manner.

As used herein, the term "avulsion," and grammatically related terms, refers to an intentionally-introduced injury in which a body structure is detached from its normal point of attachment to another body structure. The term does not require a particular type of detachment between the body structures. Indeed, the term includes any type of detachment between body structures. Non-limiting examples of types of detachment include tearing, cutting and clipping. Also, the term does not require that either of the body structures be any particular type of body structure. Indeed, each of the body structures can be any type of body structure. Non-limiting examples of types of body tissues include tissues, portions of tissue, connective tissues, nerve tissue, organs, and portions of organs. Non-limiting examples of specific avulsions include detachment of a valve leaflet from a vessel wall by tearing the valve leaflet away from the wall, cutting of synechiae, clipping of tendons, such as the chordae tendineae, and thromboectomy.

As used herein, the term "wire," and grammatically related terms, refers to a single strand of material. The term does not require a particular material. Indeed, the term includes any type of material. Non-limiting examples of types of materials include metals, including alloys, polymeric materials, natural materials, flexible materials, and stiff materials. Non-limiting examples of specific materials include stainless steel; a shape memory material, such as a nickel titanium alloy; and a plastic material, such as nylon. Combinations of materials can also be used. For examples, a metal core can be partially or completely covered by another material, such as a plastic. Also, the term does not require a particular configuration of the material. Non-limiting examples of possible configurations include rods and ribbons of materials. Also, the term does not require any particular cross-sectional shape for the material. Non-limiting examples of possible cross-sectional shapes include circular, elliptical, square and rectangular cross-sectional shapes.

FIGS. 1, 1A, 1B, 1C, 2A, and 2B illustrate an example cutting device 10. The cutting device 10 includes an elongate main body 12 extending between a proximal end 14 and a distal end 16. The main body 12 can be coiled on itself to form a loop 18. The distal end 16 defines a hook 20.

Figure 1:
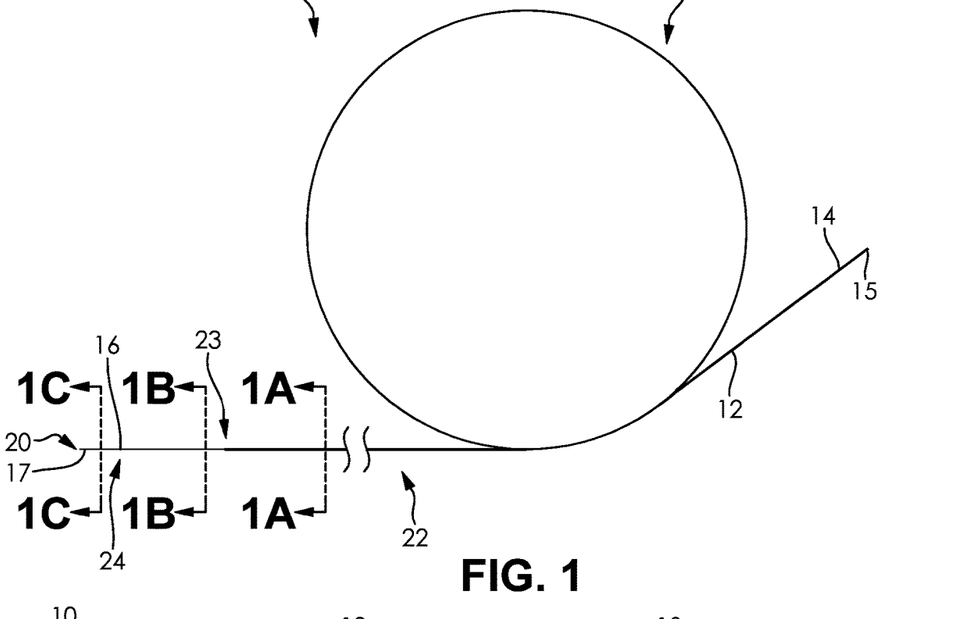
FIG. 1 is a side view of an example cutting device.
Figures 1A, 1B, 1C, 2A, 2B:
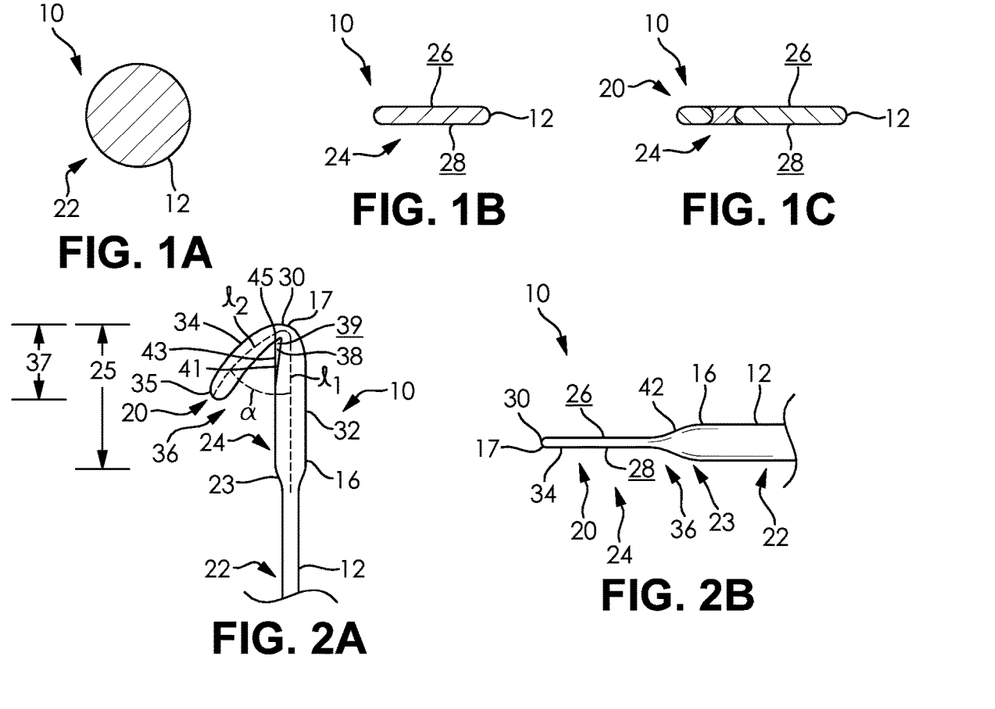
FIG. 1A is an enlarged cross-sectional view of the cutting device illustrated in FIG. 1, taken along line 1A-1A.
FIG. 1B is an enlarged cross-sectional view of the cutting device illustrated in FIG. 1, taken along line 1B-1B.
FIG. 1C is an enlarged cross-sectional view of the cutting device illustrated in FIG. 1, taken along line 1C-1C.
FIG. 2A is an enlarged top view of the distal end of the cutting device illustrated in FIG. 1.
FIG. 2B is an enlarged side view of the distal end of the cutting device illustrated in FIG. 1.

The main body 12 includes a first axial portion 22 having a circular cross-sectional shape and a second axial portion 24 having a substantially rectangular cross-sectional shape. As best illustrated in FIGS. 1B and 1C, the second axial portion 24 has first 26 and second 28 opposing surfaces. A third axial portion 23 is disposed axially between the first 22 and second 24 axial portions. As best illustrated in FIG. 2B, the third axial portion 23 defines a sloped surface 42 that transitions from the circular cross-sectional shape of the first axial portion 22 to the rectangular cross-sectional shape of the second axial portion 24. Thus, the axial first portion 22 of the main body 12 has a cross-sectional shape with no flat surfaces and the second axial portion 24 of the main body 12 has a cross-sectional shape having at least two or more flat or substantially flat surfaces.

As best illustrated in FIG. 2A, hook 20 is defined by a bend 30 in main body 12 that forms opposing first 32 and second 34 arms, each of which comprise a portion of the main body 12. In the illustrated embodiment, the second arm 34 terminates in a rounded surface 35. Inclusion of rounded surface 35 provides an atraumatic tip to the cutting device 10, which may be advantageous for cutting devices intended to be used as medical devices.

The bend 30 has angle α and forms notch 36 comprising an open space between first 32 and second 34 portions of the main body 12. A first sharpened edge 38 is disposed on the side of the first portion 32 of the main body 12 that faces the notch 36. An optional second sharpened edge, not illustrated with the first example embodiment, can be disposed on the side of the second portion 34 of the main body 12 that faces the notch 36. Accordingly, if an optional second sharpened edge is included, the sharpened edges are disposed on opposing sides of notch 36.

Inclusion of a second sharpened edge is optional. A skilled artisan will be able to determine if inclusion of a second sharpened edge is desired for a cutting device according to a particular embodiment based on various considerations, including the nature of the material with which the cutting device is intended to be used. The inventors have determined that inclusion of only a single sharpened edge, such as in the example embodiment illustrated in FIGS. 1, 1A, 1B, 1C, 2A, and 2B, is suitable and sufficient for a cutting device intended to be used for cutting biological tissue, such as chordae tendineae.

Each sharpened edge included in a cutting device according to an embodiment can have any suitable structure and relative position on the respective portion of the main body. The example cutting device 10 includes a sharpened edge 38 having a suitable structure and position. As best illustrated in FIG. 2A, the sharpened edge 38 comprises a ramped surface 39 that terminates in an interface 41 with the first surface 26 of the second portion 24 of the main body 12. Opposite interface 41, ramped surface 39 terminates in leading edge 43. At its distal end, ramped surface 39 slopes downward from interface 41 to leading edge 43 along wall portion 45, which is an extension of the inwardly-oriented side of the second arm 34 of the hook 20 and which lies on a plane that is substantially perpendicular to a plane on which the first surface 26 of the second portion 24 of the main body 12 lies. Thus, as best illustrated in FIG. 2A, the sharpened edge 38 in the example embodiment has a generally triangular shape.

The first axial portion 22 can have any suitable axial length that comprises a portion of the total axial length of the main body 12. The axial length of the first axial portion 22 is measured from the terminal surface 15 of the proximal end 14 of the main body 12 to the transverse midpoint on the sloped surface 42 of the third axial portion 23 of the main body 12. In the illustrated embodiment, the first axial portion 22 has an axial length that is about 95% of the total axial length of the main body 12. The inventors have determined that this axial length provides desirable characteristics for the cutting device 10, including ease of handling and a minimal length over which additional forming techniques need to be applied during fabrication. A skilled artisan can select a suitable axial length for a first axial portion of a main body in a cutting device according to a particular embodiment based on various considerations, including a desired size of the hook as compared to the total axial length of the main body. Examples of suitable axial lengths for a first axial portion in an embodiment include an axial length that is between about 50% and about 99% of the total axial length of the main body, an axial length that is between about 60% and about 99% of the total axial length of the main body, an axial length that is between about 70% and about 99% of the total axial length of the main body, an axial length that is between about 80% and about 99% of the total axial length of the main body, an axial length that is between about 90% and about 99% of the total axial length of the main body, an axial length that is between about 95% and about 99% of the total axial length of the main body, an axial length that is between about 96% and about 99% of the total axial length of the main body, an axial length that is between about 97% and about 99% of the total axial length of the main body, and an axial length that is between about 98% and about 99% of the total axial length of the main body.

Similarly, the second axial portion 24 can have any suitable axial length 25 that comprises a portion of the total axial length of the main body 12. As best illustrated in FIG. 2A, the axial length 25 of the second axial portion 24 is measured from the transverse midpoint on the sloped surface 42 of the third axial portion 23 of the main body 12 to the terminal surface 17 of the distal end 16 of the main body 12. In the illustrated embodiment, the second axial portion 24 has an axial length that is about 5% of the total axial length of the main body 12. The inventors have determined that this axial length provides desirable characteristics for the cutting device 10, including ease of handling and a minimal length along which additional forming techniques are applied during fabrication. A skilled artisan can select a suitable axial length for a second axial portion of a main body in a cutting device according to a particular embodiment based on various considerations, including a desired size of the hook as compared to the total axial length of the main body. Examples of suitable axial lengths for a second axial portion in an embodiment include an axial length that is between about 1% and about 50% of the total axial length of the main body, an axial length that is between about 1% and about 40% of the total axial length of the main body, an axial length that is between about 1% and about 30% of the total axial length of the main body, an axial length that is between about 1% and about 20% of the total axial length of the main body, an axial length that is between about 1% and about 10% of the total axial length of the main body, an axial length that is between about 1% and about 5% of the total axial length of the main body, an axial length that is between about 1% and about 4% of the total axial length of the main body, an axial length that is between about 1% and about 3% of the total axial length of the main body, and an axial length that is between about 1% and about 2% of the total axial length of the main body.

The hook 36 can have any suitable axial length 37 that comprises a portion of the axial length 25 of the second axial portion 24 of the main body 12. As best illustrated in FIG. 2A, the axial length 37 of the hook 36 is measured from the terminal surface 17 of the distal end 16 of the main body 12 to the transverse midpoint on the sloped surface 42 of the third axial portion 23 of the main body 12. In the illustrated embodiment, the hook 16 has an axial length 37 that is about 50% of the axial length 25 of the second axial portion 24 of the main body 12. The inventors have determined that this axial length provides desirable characteristics for the cutting device 10, including stability of the hook 16. A skilled artisan can select a suitable axial length for a hook in a cutting device according to a particular embodiment based on various considerations, including a desired size of the hook. Examples of suitable axial lengths for a hook in an embodiment include an axial length that is between about 5% and about 95% of the axial length of the second axial portion of the main body, an axial length that is between about 10% and about 90% of the axial length of the second axial portion of the main body, an axial length that is between about 20% and about 80% of the axial length of the second axial portion of the main body, an axial length that is between about 30% and about 70% of the axial length of the second axial portion of the main body, an axial length that is between about 40% and about 60% of the axial length of the second axial portion of the main body, and an axial length that is between about 45% and about 55% of the axial length of the second axial portion of the main body.

The hook 20 can define any suitable has angle α. As best illustrated in FIG. 2A, the angle α of the hook 20 is measured between the lengthwise axis $l_1$ of the first arm 32 and the lengthwise axis $l_2$ of the second arm 34. In the illustrated embodiment, the angle α is about 45°. The inventors have determined that this angle provides desirable characteristics for the cutting device 10, including a desired balance between access to the sharpened edges 38, 40 inside the notch 36 and protection from unwanted exposure to the sharpened edges 38, 40. A skilled artisan can select a suitable angle for a hook in a cutting device according to a particular embodiment based on various considerations, including the size of the body structure with which the cutting device is intended to be used. Examples of suitable angles for a hook in an embodiment include an angle that is between about 10° and about 90°, an angle that is between about 20° and about 80°, an angle that is between about 30° and about 70°, an angle that is between about 40° and about 60°, an angle that is between about 40° and about 50°, an angle that is about 90°, an angle that is about 60°, an angle that is about 45°, and an angle that is about 30°.

In the illustrated embodiment, the cutting device 10 includes only a single sharpened edge 38. It is noted, though, that any suitable number and arrangement of sharpened edges can be included in a cutting device according to a particular embodiment and a skilled artisan will be able to select an appropriate number of sharpened edges for a cutting device according to a particular embodiment based on various considerations, including the nature, size and overall configuration of the body structure with which the cutting device is intended to be used and the nature of the material forming the cutting device. Examples of suitable numbers and arrangements of sharpened edges include a single sharpened edge that extends on both the first and second arms of the hook, first and second sharpened edges disposed on opposing sides of the hook and separated by a non-sharpened surface, such as a non-sharpened surface disposed in a bend positioned between the first and second arms, a series of sharpened edges with non-sharpened surfaces disposed between the individual sharpened edges of the series of sharpened edges, and first and second series of sharpened edges with non-sharpened surfaces disposed between the individual sharpened edges of each of the first and second series of sharpened edges.

The structure of cutting device 10 provides two levels of control over that which can and cannot be cut by the cutting device 10. As a first level of control, the length of the second arm 34 and angle α cooperatively limit the size of objects and materials that can fit within the open space of the notch 36. If an object or item does not fit within the open space of the notch 36, it cannot contact the cutting edge 38 and, as a result, cannot be cut by the cutting device 10. As a second level of control, the size of the sharpened edge 38, and the length of the leading edge 43 in particular, define the maximum length along which an object or material that fits within the open space of the notch 36 can be cut. If the object or material has a dimension that is less than the length of the leading edge 43, the cutting device 10 will be able to fully cut the object or material into separate pieces, assuming the cutting edge 38 can cut through the object or material. However, if the object or material fits within the open space of the notch 36 but lacks a dimension that is less than the length of the leading edge 43, the cutting device 10 will not be able to fully cut the object or material into separate pieces and will likely only be able to nick the object or material, which may be desirable. By varying these components of the structure of the cutting device, a skilled artisan will be able to make a cutting device according to an embodiment that provides desirable cutting properties for a particular object or material.

Figure 3:
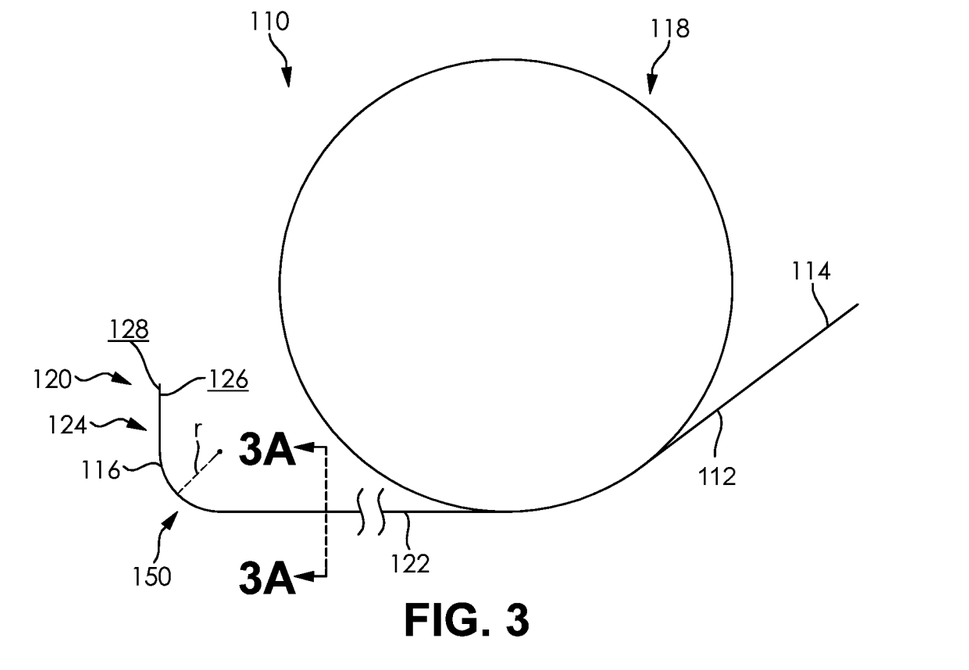
FIG. 3 is a side view of another example cutting device.
Figure 3A:
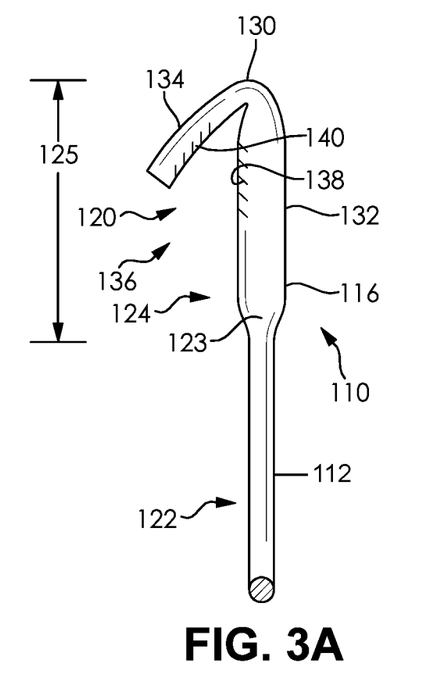
FIG. 3A is an enlarged cross-sectional view of the cutting device illustrated in FIG. 3, taken along line 3A-3A.

FIGS. 3 and 3A illustrate another cutting device 110. The cutting device 110 is similar to the cutting device 10 illustrated in FIG. 1 and described above, except as detailed below. Thus, the cutting device 110 includes an elongate main body 112 extending between a proximal end 114 and a distal end 116. The main body 112 can be coiled on itself to form a loop 118. The distal end 116 defines a hook 120. The main body 112 includes a first axial portion 122 having a circular cross-sectional shape and a second axial portion 124 having a substantially rectangular cross-sectional shape. The second axial portion 124 has first 126 and second 128 opposing and flat surfaces. A third axial portion 123 is disposed axially between the first 122 and second 124 axial portions. Hook 120 is defined by a bend 130 in main body 112 that forms opposing first 132 and second 134 arms, each of which comprise a portion of the main body 112. The bend 130 forms notch 136 comprising an open space between first 132 and second 134 portions of the main body 112. A first sharpened edge 138 is disposed on the side of the first portion 132 of the main body 112 that faces the notch 136. Similarly, a second sharpened edge 140 is disposed on the side of the second portion 134 of the main body 112 that faces the notch 136. In this embodiment, each of the first 138 and second 140 sharpened edges comprises a ramped surface extending from a leading edge to an interface with a portion of the main body 112.

In this embodiment, as best illustrated in FIG. 3, main body 112 includes a pre-defined curve 150 that is disposed proximal of the distal end 116 of the main body 112. Inclusion of a pre-defined curve in a cutting device according to an embodiment may be advantageous for cutting devices intended to be used on tissues or in locations that require navigation of a tortuous path to achieve the desired avulsion. If included, the pre-defined curve can have any suitable size and configuration. In the illustrated embodiment, as best shown in FIG. 3, pre-defined curve 150 has radius of curvature r that is about 200% of the axial length 125 of the second axial portion 124 of the main body 112. The inventors have determined that this radius of curvature provides desirable characteristics for a cutting device intended for clipping chordae tendineae. A skilled artisan can select a suitable radius of curvature for a pre-defined curve in a cutting device according to a particular embodiment based on various considerations, including the size, nature, location and access route of the body structure with which the cutting device is intended to be used. Examples of suitable radii of curvature for a pre-defined curve in an embodiment include a radius of curvature that is between about 25% and about 500% of the axial length of the second axial portion of the main body, a radius of curvature that is between about 50% and about 400% of the axial length of the second axial portion of the main body, a radius of curvature that is between about 75% and about 300% of the axial length of the second axial portion of the main body, a radius of curvature that is between about 100% and about 200% of the axial length of the second axial portion of the main body, a radius of curvature that is about 100% of the axial length of the second axial portion of the main body, a radius of curvature that is about 125% of the axial length of the second axial portion of the main body, a radius of curvature that is about 150% of the axial length of the second axial portion of the main body, a radius of curvature that is about 175% of the axial length of the second axial portion of the main body, and a radius of curvature that is about 200% of the axial length of the second axial portion of the main body.

If included, the pre-defined curve can have any suitable structural arrangement relative to other portions of the cutting device. In the illustrated embodiment, as best shown in FIG. 3, the pre-defined curve 150 is contained within a first plane that is different than a second plane that contains the hook 120. In FIG. 3, the first plane is the plane of the drawing sheet and the second plane is a plane that is disposed perpendicular to the first plane. The inventors have determined that this structural arrangement provides desirable characteristics for a cutting device intended for clipping chordae tendineae. Also, the inventors have determined that this structural arrangement provides a cutting device that is suitable for cutting objects or materials that extend generally parallel to the elongate main body. In these embodiments, rotation of the main body on the lengthwise axis of the main body results in rotation of the hook of the cutting device in a manner that catches the object or material to be cut. Pulling on the elongate main body after catching the object or material results in cutting of the object or material, even when the object or material extends generally parallel to the elongate main body.

A skilled artisan can select a suitable structural arrangement for a pre-defined curve in a cutting device according to a particular embodiment based on various considerations, including the size, nature, location and access route of the body structure with which the cutting device is intended to be used. Examples of suitable structural arrangement for a pre-defined curve in an embodiment include a structural arrangement in which the pre-defined curve is contained on a first plane that is different from a second plan that contains the hook of the cutting device, a structural arrangement in which the pre-defined curve is contained on a first plane that is perpendicular to a second plane that contains the hook, a structural arrangement in which the pre-defined curve is contained on a first plane that is substantially perpendicular to a second plane that contains the hook, and a structural arrangement in which the pre-defined curve is contained on a plane that also contains the hook.

Figure 4:
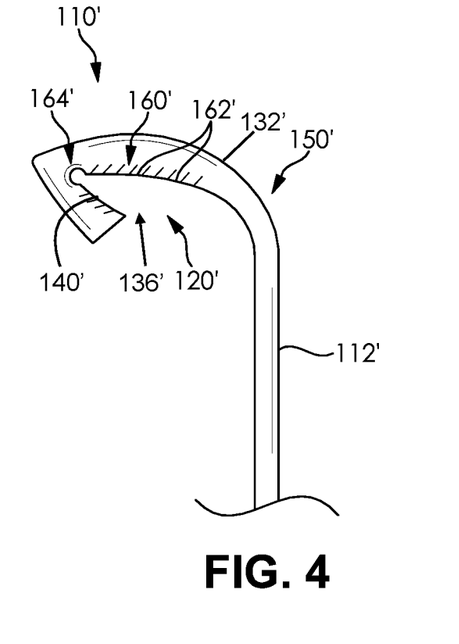
FIG. 4 is an enlarged top view of the distal end of an example alternative cutting device.

FIG. 4 illustrates the distal end of an example alternative cutting device 110' in which the pre-defined curve 150' is disposed on a plane that also contains the hook 120'. In FIG. 4, the plane that contains the pre-defined curve 150' and the hook 120' is the plane of the drawing sheet. In this alternative embodiment, the first arm 132' defines a series of sharpened edges 160' with non-sharpened surfaces 162' disposed between pairs of sharpened edges of the series of sharpened edges 160'. The second arm 134 defines a single sharpened edge 140'. Also, the main body 112' defines an enlarged opening 164' at the base of the notch 136'. Inclusion of an enlarged opening 164' may enhance engagement of body structures and/or provide a degree of tactile feedback during use of the cutting device 110'.

The cutting devices can be made from any suitable material. Skilled artisans will be able to select an appropriate material for a cutting device according to a particular embodiment based on various considerations, including the nature of the avulsion the cutting device is intended to create. Examples of suitable materials include metals, plastics and other polymeric materials, other materials used in the manufacture of conventional cutting devices, and newly-developed materials determined to be suitable for use in cutting devices. Stainless steel is considered advantageous at least because of its well-characterized nature, wide acceptance as a material for use in cutting devices that contact body structures, workable nature, and other factors. The inventors have determined that use of a stainless steel rod having a circular or substantially circular cross-sectional shape is particularly advantageous. Use of stainless steel, however, is considered optional and a skilled artisan may determine that another material is desirable or advantageous for us in a cutting device according to a particular embodiment.

The cutting devices can be fabricated in any suitable manner and using any suitable technique. Skilled artisans will be able to select an appropriate technique for fabricating a cutting device according to a particular embodiment based on various considerations, including the nature of the material used for cutting device. Example techniques that can be used in the fabrication of a cutting device according to an embodiment include extruding, casting, and forging.

Figure 5:
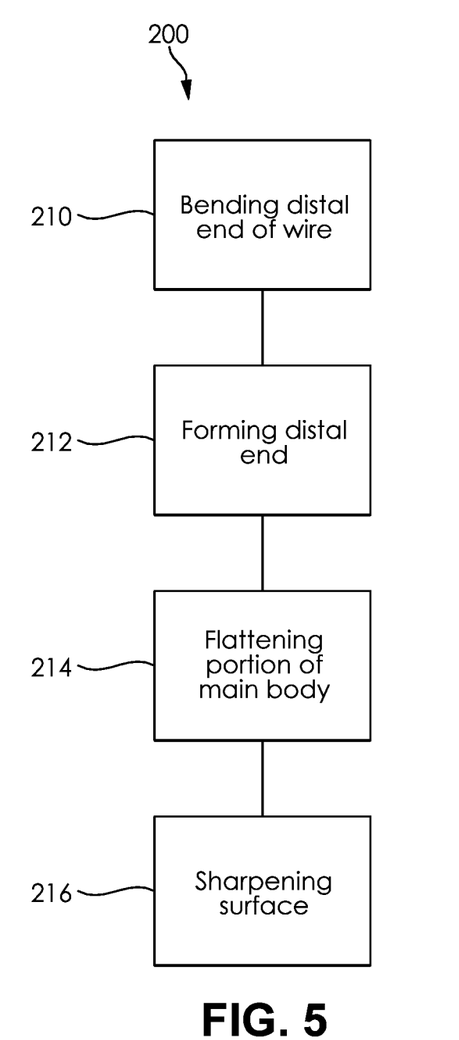
FIG. 5 is a flowchart illustration of an example method of making a cutting device.

The inventors have developed methods of making cutting devices according to an embodiment. FIG. 5 is a flowchart illustration of an example method 200 of making a cutting device. An initial step 210 comprises bending a distal end of a wire having a main body, a proximal end and a distal end such that a distal tip defining an angle is formed. Another step 212 comprises forming the distal end such that the angle of the distal tip changes to form a hook having first and second opposing arms. Another step 214 comprises flattening a portion of the main body that includes the hook. Another step 216 comprises sharpening a surface on the inside of the hook. An optional step can include sharpening another surface on the inside of the hook.

Step 210 can be accomplished using any suitable technique and to any suitable degree. For example, for stainless steel wires, bending the distal end of a wire by hand or with a simple hand tool, such as a pair of pliers, is suitable. Also, any suitable angle can be achieved as a result of this step. If a roll-forming technique is used in step 214, as described below, the inventors have determined that an angle that is between about 175° and about 180° is suitable. An angle that is substantially 180° is also considered suitable, and can be achieved by bending the wire back on itself as much as possible.

Step 212 can be accomplished using any suitable technique and to any suitable degree. For example, the distal end can be formed by hand or with a suitable hand tool. In most methods, it will be desirable to form the distal end such that the angle of the distal tip lessens. For example, the angle can be changed from the angle achieved in step 210 to a smaller angle of about 135°, which would provide a desirable hook angle of about 45°, as described above.

Step 214 can be accomplished using any suitable technique and to any suitable degree. For example, the distal end can be hammered flat or can be passed through rollers such that it is roll-formed to a flat configuration. Roll-forming is considered advantageous at least because it enables steps 212 and 214 to be conducted simultaneously. For example, when the distal end is passed through rollers to flatten it, the distal tip responds by opening a bit to form the hook. While considered advantageous, simultaneous performance of steps 212 and 214 is optional.

In an example method, step 214 comprises repeatedly passing the distal end through rollers. For example, in one example method, the distal end is passed through rollers multiple times. In one example method, the separating distance between the rollers is reduced before each subsequent pass of the distal end through the rollers. This provides a gradual reduction in the thickness of the distal end of the device, which provides desirable characteristics for the resulting cutting device.

Step 216 can be accomplished using any suitable technique. Examples of suitable techniques include grinding and etching. A skilled artisan will be able to select a suitable sharpening technique for a method according to a particular embodiment based on various considerations, including the nature of the material of the wire. The inventors have determined that one or more passes of a whetstone across the surface of the wire is a suitable sharpening technique for methods in which the wire comprises a metal.

Various additional optional steps can be included in a particular method. For example, if it is desired to include an atraumatic tip on the distal end of the cutting device, an additional step of rounding an end of the wire can be included. If included, a rounding step can be accomplished using any suitable technique, such as be grinding the end to form a rounded surface, and can be performed at any suitable point in the method, including before or after step 210. Also, a step of buffing a portion of the distal end can be included. If included, the buffing step is advantageously done until a mirror finish is achieved, and is advantageously performed prior to the step 216 of sharpening a surface. A step of electropolishing the distal end can be included. If included the electropolishing step is advantageously performed after the step 216 of sharpening a surface.

Also, an additional step of altering the length of one of the first and second opposing arms of the hook formed by performance of step 212 can be included. If included, this step can be accomplished using any suitable technique, such as cutting the arm to a shorter length.

Figure 6:
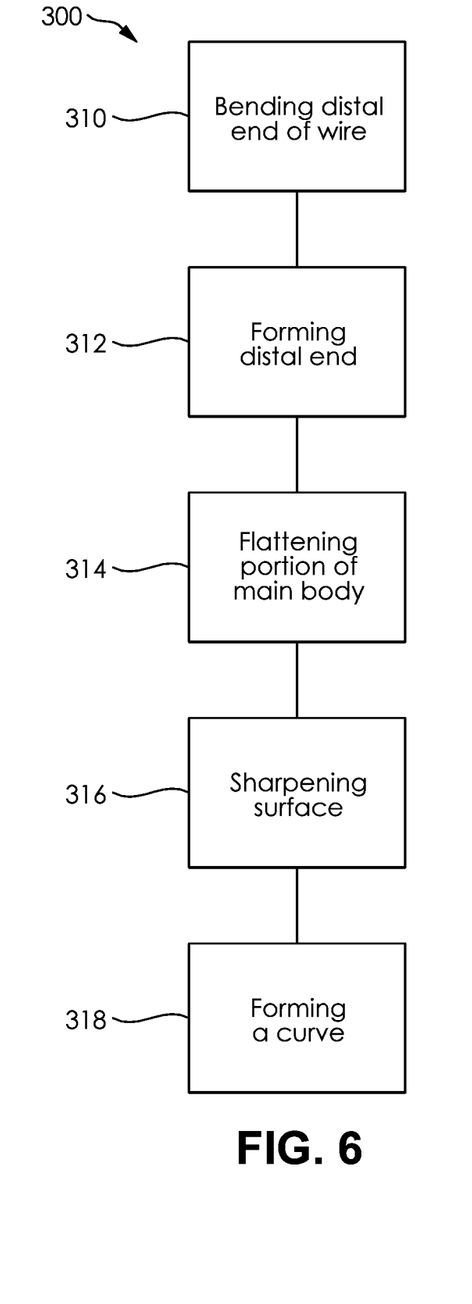
FIG. 6 is a flowchart illustration of another example method of making a cutting device.

FIG. 6 is a flowchart illustration of another example method 300 of making a cutting device. An initial step 310 comprises bending a distal end of a wire having a main body, a proximal end and a distal end such that a distal tip defining an angle is formed. Another step 312 comprises forming the distal end such that the angle of the distal tip changes to form a hook. Another step 314 comprises flattening a portion of the main body that includes the hook. Another step 316 comprises sharpening a surface on the inside of the hook. Another step 318 comprises forming a curve in the wire at a point proximal of the distal end of the wire.

Steps 310, 312, 314, 316 can be accomplished using any suitable technique, including those described above in connection with method 200 illustrated in FIG. 5. Step 318 can be also be accomplished using any suitable technique, including bending a portion of the wire with a hand tool or shaping a portion of the wire with a roller.

EXAMPLE

Figure 7:
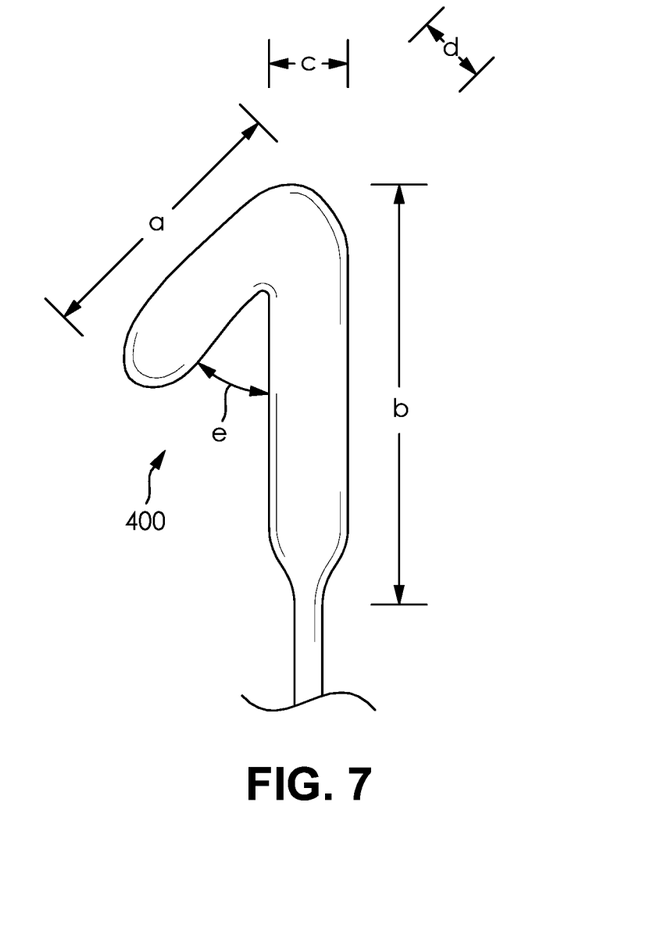
FIG. 7 is an enlarged top view of the distal end of another example cutting device.

FIG. 7 illustrates the distal end of an example cutting device 400 with various dimensional references. As described above, a cutting device according to and embodiment can have any suitable dimensions. The following provides examples of various dimensions and dimensional ratios the inventors have determined to be suitable for cutting devices according to a particular embodiment that is well-suited for clipping chordae tendineae.

A suitable length for length a is between about 0.05" and about 0.2". A length of between about 0.0625" and about 0.125" is also suitable for length a. A length of about 0.1" is also considered suitable for length a.

A suitable length for length b is between about 0.2" and 2". A length of between about 0.2" and about 0.5" is also suitable for length b. A length of about 0.25" is also considered suitable for length b.

A suitable sum of widths c and d is between about 0.01" and about 0.05". A sum of between about 0.025" and about 0.035" is also suitable for the sum of widths c and d. A sum of about 0.030" is also considered suitable for the sum of widths c and d.

A suitable ratio of lengths a and b is between about 1:2 and about 1:4.

A suitable angle for angle e is between about 15° and about 50°. An angle of between about 25° and about 35° is also considered suitable for angle e. An angle of about 30° is also considered suitable for angle e.

Those with ordinary skill in the art will appreciate that various modifications and alternatives for the described and illustrated embodiments can be developed in light of the overall teachings of the disclosure. Accordingly, the particular structures and methods disclosed are intended to be illustrative only and not limiting as to the scope of the invention, which is to be given the full breadth of the claims and any and all equivalents thereof.

We claim:

1. A method of making a cutting device, the method comprising:
    bending a distal end of a wire having a main body, a proximal end and the distal end such that a distal tip defining an angle is formed;
    forming the distal end such that the angle of the distal tip changes to form a hook defined by a bend and having first and second opposing arms;
    flattening a portion of the main body that includes the hook;
    sharpening a surface on an inside of the hook; and
    forming a curve in the wire at a point proximal of the distal end of the wire;
    wherein the curve is contained in a first plane and the hook is contained in a second, different plane;
    wherein the first opposing arm extends from the bend toward the curve along the first plane; and
    wherein the second opposing arm extends from the bend away from the first opposing arm along the second plane.

2. The method of claim 1, wherein the second plane is disposed perpendicular or substantially perpendicular to the first plane.

3. The method of claim 1, further comprising altering the length of one of the first and second opposing arms.

4. The method of claim 1, wherein forming the distal end comprises forming the distal end such that the angle of the distal tip changes to about 135 degrees to form the hook.

5. The method of claim 1, wherein flattening the portion of the main body that includes the hook is accomplished by roll-forming the portion of the main body that includes the hook.

6. The method of claim 5, wherein bending the distal end of the wire comprises bending the distal end of the wire such that the distal tip defining an angle between about 175 degrees and about 180 degrees is formed.

7. The method of claim 6, wherein forming the distal end comprises forming the distal end such that the angle of the distal tip changes to about 135 degrees to form a hook.

8. The method of claim 1, wherein forming the distal end and flattening the portion of the main body are conducted simultaneously.

9. The method of claim 1, wherein sharpening the surface on the inside of the hook is accomplished by grinding.

10. The method of claim 1, wherein sharpening the surface on the inside of the hook is accomplished by etching.

11. The method of claim 1, further comprising rounding the distal end of the wire.

12. The method of claim 1, further comprising buffing a portion of the distal end of the wire.

13. The method of claim 1, further comprising electropolishing the distal end of the wire.

14. The method of claim 13, wherein electropolishing the distal end of the wire is performed after sharpening the surface on the inside of the hook.

15. The method of claim 1, wherein the curve extends along a first axial portion of the main body having a first cross-sectional shape; and
wherein the hook extends along a second axial portion of the main body having a second cross-sectional shape that is different than the first cross-sectional shape.

16. A method of making a cutting device, the method comprising:
bending a distal end of a wire having a main body, a proximal end and the distal end such that a distal tip defining an angle is formed;
forming the distal end such that the angle of the distal tip changes to form a hook defined by a bend and having first and second opposing arms;
flattening a portion of the main body that includes the hook;
sharpening a first surface on an inside of the hook;
sharpening a second surface on the inside of the hook; and
forming a curve in the wire at a point proximal of the distal end of the wire;
wherein the curve is contained within in a first plane and the hook is contained in a second, different plane;
wherein the first opposing arm extends from the bend toward the curve along the first plane; and
wherein the second opposing arm extends from the bend away from the first opposing arm along the second plane.

17. A method of making a cutting device, the method comprising:
bending a distal end of a wire having a main body, a proximal end and the distal end such that a distal tip defining an angle is formed;
forming the distal end such that the angle of the distal tip changes to form a hook defined by a bend and having first and second opposing arms;
flattening a portion of the main body that includes the hook;
sharpening a first surface on an inside of the hook;
sharpening a second surface on the inside of the hook; and
forming a curve in the wire at a point proximal of the distal end of the wire;
wherein the curve is contained within in a first plane and the hook is contained in a second, different plane, the second plane disposed perpendicular or substantially perpendicular to the first plane;
wherein the first opposing arm extends from the bend toward the curve along the first plane; and
wherein the second opposing arm extends from the bend away from the first opposing arm along the second plane.

* * * * *